United States Patent [19]

de Loos-Vollebregt

[11] Patent Number: 4,917,493

[45] Date of Patent: Apr. 17, 1990

[54] FURNACE FOR ELECTROTHERMAL ATOMIZATION OF SAMPLES FOR ANALYSIS BY ATOMIC ABSORPTION SPECTROPHOTOMETRY

[75] Inventor: Margaretha T. C. de Loos-Vollebregt, Pynacker, Netherlands

[73] Assignee: The Perkin-Elmer Corporation, Norwalk, Conn.

[21] Appl. No.: 205,888

[22] Filed: Jun. 13, 1988

[30] Foreign Application Priority Data

Jun. 19, 1987 [DE] Fed. Rep. of Germany ....... 3720376

[51] Int. Cl.$^4$ ............................................ G01N 21/74
[52] U.S. Cl. ................................................... 356/312
[58] Field of Search ..................... 356/311, 312, 244

[56] References Cited

U.S. PATENT DOCUMENTS 4,407,582 10/1983 Woodriff ............................. 356/312
4,579,451 4/1986 Lersmacher ......................... 356/312

FOREIGN PATENT DOCUMENTS 2949275 6/1981 Fed. Rep. of Germany .

OTHER PUBLICATIONS

Chakrabarti et al., "Capacitive Discharge Heating in Graphite Furnace Atomic Absorption Spectrometry", Anal. Chem., vol. 52, No. 1, Jan. 1980, pp. 167–176.

Primary Examiner—Vincent P. McGraw
Attorney, Agent, or Firm—Thomas P. Murphy; Edwin T. Grimes

[57] ABSTRACT

An electrically heated tubular body fabricated of pyrolytic graphite in coaxial layers serves to atomize samples for analysis by atomic absorption apectrophotometry. Radially extending graphite rods engage the medial portion of the tubular body at diametrically opposed locations and constitute electrodes for passing an electric heating current transversely through the body. Owing to the characteristic anisotropy of electrical and thermal conductivity of the graphite layers, a relatively high electrical resistance to the current and an even temperature distribution along the length of the tubular body result.

2 Claims, 1 Drawing Sheet

FURNACE FOR ELECTROTHERMAL ATOMIZATION OF SAMPLES FOR ANALYSIS BY ATOMIC ABSORPTION SPECTROPHOTOMETRY

Background of the Invention

1. Field of the Invention

This invention relates, in general, to atomic absorption spectrophotometry (AAS) and, more particularly, to electrothermal atomizers or so-called graphite furnaces for atomizing samples in connection with atomic absorption spectrophotometric analysis thereof.

2. Description of Related Art

Conventionally, graphite atomizers comprise a graphite tube having its ends engaged by annular electrode members through which it is supplied with an electric heating current to cause resistance heating of the tube. Normally, heating is effected in three, progressively higher stages to dry, then ash, and finally atomize the sample which is introduced through a small port in the side wall of the tube at the midpoint of its length.

When constructed of spectral graphite, the tubes have low heating rates and exhibit temperature gradients along their length, the ends being cooler. This temperature variation is exacerbated by the dissipation of heat to the electrodes at the ends of the tube. As a result, sample vapor tends to condense at the ends of the tube and reevaporate in subsequent usage, contaminating the new sample and degrading analytical data obtained.

It is known in the art to fabricate graphite tubes entirely from pyrolytic graphite. Owing to the manner of its production, pyrolytic graphite (also known as oriented graphite) has a lamellar structure in consequence of which the material exhibits anisotropy of its electrical and thermal conductivity. More specifically, both electrical and thermal conductivity are very much higher in the plane of the lamellas than in a plane perpendicular thereto.

As described in *Analytical Chemistry*, 52 (1980) at pages 167–176, the tube is machined from a block of pyrolytic graphite consisting of plane, parallel lamellas, so that the tube axis is parallel to the planes of the lamellas. Heating current is supplied transversely to the tube axis by means of electrodes engaging the sidewalls of the tube. In the machining operation the lamellas are cut and, as a result, the tube has no defined conductivity condition.

Also known in the art, as described in DE-OS 2 949 275, are graphite tubes composed entirely of pyrolytic graphite and having hollow cylindrical lamellas coaxial with the tubes.

With the foreoing state of the art in view, it is the general object of the present invention to provide a transversely heated tubular graphite furnace for electrothermal atomization of samples for analysis by atomic absorption spectrophotometry which overcomes or at least mitigates the shortcomings of the prior art.

A specific object is to provide a tubular graphite furnace of the type alluded to in the preceding general object which, in use, exhibits a substantially uniform temperature along its entire length.

Another object is the provision of a tubular graphite furnace which presents a relatively high electric resistance to heating current, thus enabling the use of higher operating voltages with lower current and rendering transition resistances non-critical.

Still another object of the invention is to achieve a graphite furnace in accordance with the preceding objects in which the heating and heat capacity of the electrodes are reduced in comparison with comparable prior art furnaces.

SUMMARY OF THE INVENTION

To the attainment of these and other objects and advantages which will become apparent as this description proceeds, the invention contemplates an electrothermal graphite furnace for atomization of samples for analysis by atomic absorption comprising a tubular body fabricated entirely of pyrolytic graphite formed in coaxially cylindrical layers, and electrodes extending radially from the tubular body for passing a heating current transversely therethrough. The electrodes engage the tubular body only at diametrically opposite points at the midsection thereof and extend radially outward with respect to the axis of the tubular body.

With this construction the pyrolytic graphite has a relatively high electrical resistivity for the transversely flowing electrical heating current; this enables the use of higher voltages and lower heating current with a consequent reduction in electrode heating. In addition, transition resistance between the electrodes and the furnace are rendered less critical.

Concomitently, in the longitudinal direction of the tubular body, thermal conductivity is high, resulting in rapid temperature equalization. This effect is enhanced by the fact that there is no dissipation of heat to the electrodes at the ends of the tube as is the case in conventional graphite furnaces.

Preferred Embodiment of the Invention

Figure 1:
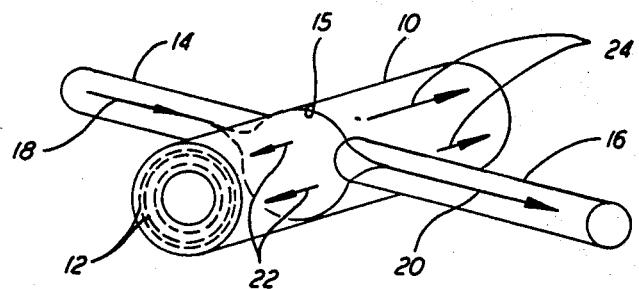
FIG. 1 is a schematic perspective elevational view of a tubular furnace embodying the present invention.

Referring to the drawings and first, in particular, to FIG. 1, numeral 10 designates a tubular body fabricated entirely of pyrolytic graphite. Body 10 is composed of a plurality of lamellas 12 cylindrical in form and coaxial with and defining the longitudinal axis of the tube. To enable electrothermal atomization of a sample, body 10 is provided with a pair of rod-shaped graphite electrode members 14 and 16, each having one end engaging the body only at respective diametrically opposed points on the midsection thereof.

Electrode members 14, 16 are connected to a source (not shown) of electric power. Electric current flows through the electrodes 14, 16 and transversely through body 10, as indicated by arrows 18 and 20, "Joule" heating the medial portion thereof. Heat is distributed along the length of body 10 by thermal conduction as indicated by arrows 22 and 24. A small port 15 in the sidewalls of body 10 enables introduction of a sample into the interior of the body.

Typical dimensions of the graphite furnace 10 may be 18 mm in length; an outer diameter (O.D.) of 5.6 mm;

and a wall thickness of 0.25 mm. The distance between the free ends of electrode members is 26 mm in the exemplary embodiments. Functional parameters for a furnace of these dimensions will be given presently with reference to FIGS. 2 and 3, as well as for a furnace having the same tube length and distance between the ends of the electrode rods but an O.D. of 7.9 mm and a wall thickness of 0.6 mm with reference to FIGS. 4 and 5.

Figure 3:
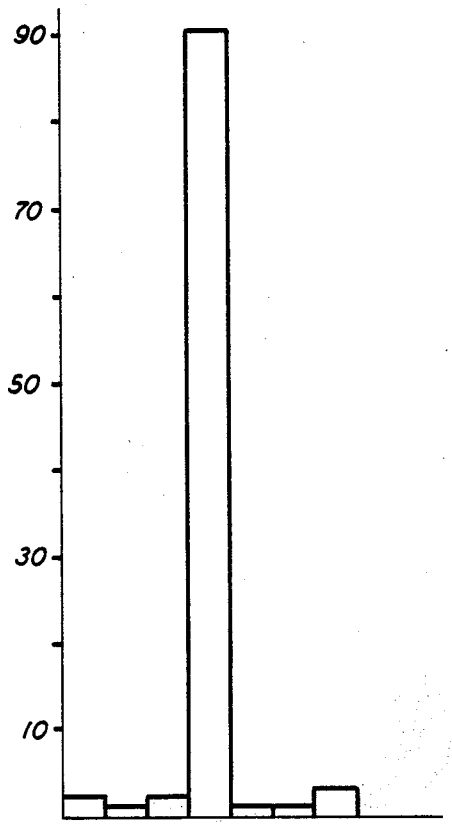
FIGS. 3 and 5 are graphic presentations correlating with FIGS. 2 and 4, respectively, to show the energy consumption distribution by the tubes and electrodes of the graphite furnace.
Figure 2:
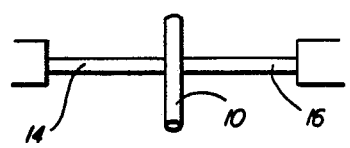
FIGS. 2 and 4 are essentially identical schematic plan views of graphite furnaces embodying the invention, differing only in the matter of dimensions and employed to graphically depict the distribution of energy consumption.

Referring then to FIGS. 2 and 3, the figures are placed in juxtaposition so that the schematic representation of the graphite furnace in FIG. 2 underlies the graph in FIG. 3. The electrode rods 14 and 16 are disposed to represent the abscissa for the graph constituting FIG. 3. In this embodiment, the energy consumption was about 60% of a conventional, longitudinally-heated graphite furnace. The temperature distribution along the length of tubular body 10 was uniform to within 100 degrees C. at an equilibrium temperature of 1000 degrees C. At an equilibrium temperature of 2000 degrees C. the temperature of tubular body 10 was uniform to within 170 degrees C. over its entire length.

FIG. 3 shows the distribution of energy consumption along the graphite rods constituting electrodes 14, 16. It can be seen that 90% of the energy consumption occurs in the graphite body 10 and only 5% in the electrode members 14, 16.

Figure 5:
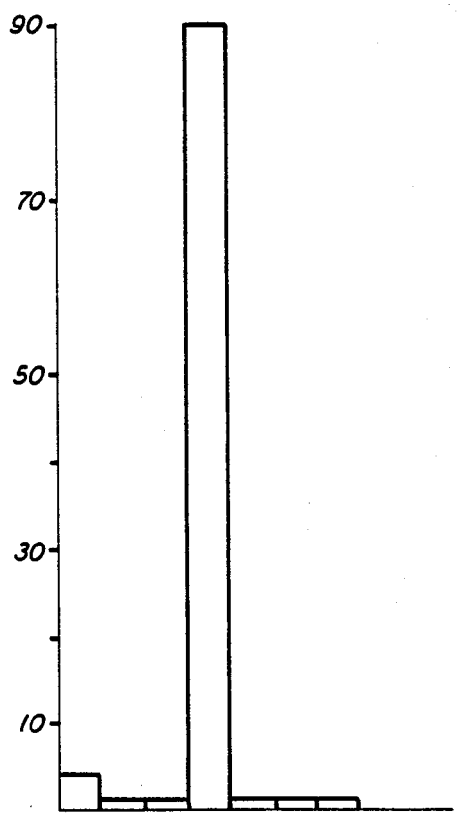
Figure 4:
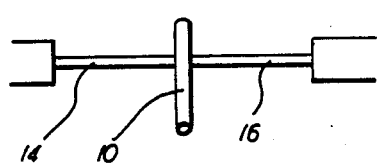

As previously mentioned, FIGS. 4 and 5 are comparable to FIGS. 3 and 4 but refer to a dimensionally different embodiment, viz., an O.D. of 7.9 mm and wall thickness of 0.6 mm. In this embodiment also, the primary energy consumption, 90%, occurred in body 10 and only 5% each in the electrodes 14, 16 and transition resistances.

While there have been described what at present are believed to be the preferred embodiments of this invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. An electrothermal graphite furnace for atomization of samples for analysis by means of atomic absorption spectrophotometry comprising:

a tubular body fabricated entirely of pyrolytic graphite formed in coaxial cylindrical lamellas; and electrode means extending radially from said body for passing electric heating current transversely therethrough.

2. An electrothermal graphite furnace for atomization of samples for analysis by means of atomic absorption spectrophotometry comprising:

a tubular body fabricated entirely of pyrolytic graphite formed in coaxial cylindrical layers; and electrode means for passing an electric heating current transversely through said tubular body, said means comprising graphite rods engaging said body only at diametrically opposite points at the midsection thereof and extending radially outward with respect to the axis of said tubular body.

* * * * *